(12) United States Patent
Ozaki et al.

(10) Patent No.: US 7,467,930 B2
(45) Date of Patent: Dec. 23, 2008

(54) MAGNETICALLY LEVITATED PUMP UTILIZING MAGNETIC BEARINGS

(75) Inventors: Takayoshi Ozaki, Iwata (JP); Kenichi Suzuki, Iwata (JP)

(73) Assignees: NTN Corporation, Osaka (JP); Terumo Kabushiki Kaisha, Tokyo (JP)

( * ) Notice: Subject to any disclaimer, the term of this patent is extended or adjusted under 35 U.S.C. 154(b) by 494 days.

(21) Appl. No.: 10/968,931

(22) Filed: Oct. 21, 2004

(65) Prior Publication Data

US 2005/0089422 A1 Apr. 28, 2005

(30) Foreign Application Priority Data

Oct. 23, 2003 (JP) ............... 2003-363607

(51) Int. Cl.
*F04B 17/00* (2006.01)
*F04B 35/04* (2006.01)

(52) U.S. Cl. ............... 417/423.14; 417/420; 417/423.7; 417/423.12

(58) Field of Classification Search ............... 417/420, 417/423.1, 423.7, 423.12, 423.14; 310/90.5
See application file for complete search history.

(56) References Cited

U.S. PATENT DOCUMENTS

| | | | | |
|---|---|---|---|---|
| 5,121,605 A | * | 6/1992 | Oda et al. | ............... 60/608 |
| 5,686,772 A | * | 11/1997 | Delamare et al. | ............ 310/90.5 |
| 6,177,745 B1 | * | 1/2001 | Narita et al. | ............ 310/156.53 |
| 6,227,817 B1 | | 5/2001 | Paden | |
| 6,394,769 B1 | | 5/2002 | Bearnson et al. | |
| 6,626,644 B2 | | 9/2003 | Ozaki | |
| 6,840,735 B2 | * | 1/2005 | Yaegashi et al. | ............... 415/42 |
| 7,070,398 B2 | * | 7/2006 | Olsen et al. | ................. 417/353 |
| 7,141,966 B2 | * | 11/2006 | Sumiya et al. | ......... 324/207.25 |

FOREIGN PATENT DOCUMENTS

| | | |
|---|---|---|
| EP | 0 378 251 A1 | 7/1990 |
| JP | 2002-130177 | 5/2002 |
| WO | WO 99/12587 | 3/1999 |
| WO | WO 99/53974 | 10/1999 |

* cited by examiner

*Primary Examiner*—Devon Kramer
*Assistant Examiner*—Patrick Hamo
(74) *Attorney, Agent, or Firm*—McDermott Will & Emery LLP (57) ABSTRACT

In a magnetically levitated pump, an impeller-side ferromagnetic body (second ferromagnetic body) provided on a circumferential surface of an impeller facing a casing unit on the side of a position sensor and a casing-side ferromagnetic body (third ferromagnetic body) opposite to the impeller-side ferromagnetic body (second ferromagnetic body) to attract the impeller toward the casing unit on the side of the position sensor are adapted to have opposite portions of mutually different shapes, so that the maximum required attractive force of an electro-magnet for magnetic bearing is suppressed and length of the electro-magnet for magnetic bearing is made shorter.

12 Claims, 9 Drawing Sheets

MAGNETICALLY LEVITATED PUMP UTILIZING MAGNETIC BEARINGS

BACKGROUND OF THE INVENTION

1. Field of the Invention

The present invention relates to a magnetically levitated pump and, more specifically, to a clean pump utilizing a magnetic bearing, which is used, by way of example, in a medical instrument such as an artificial heart.

2. Description of the Background Art

[First Prior Art Example (Description of FIG. 11)]

Figure 11:
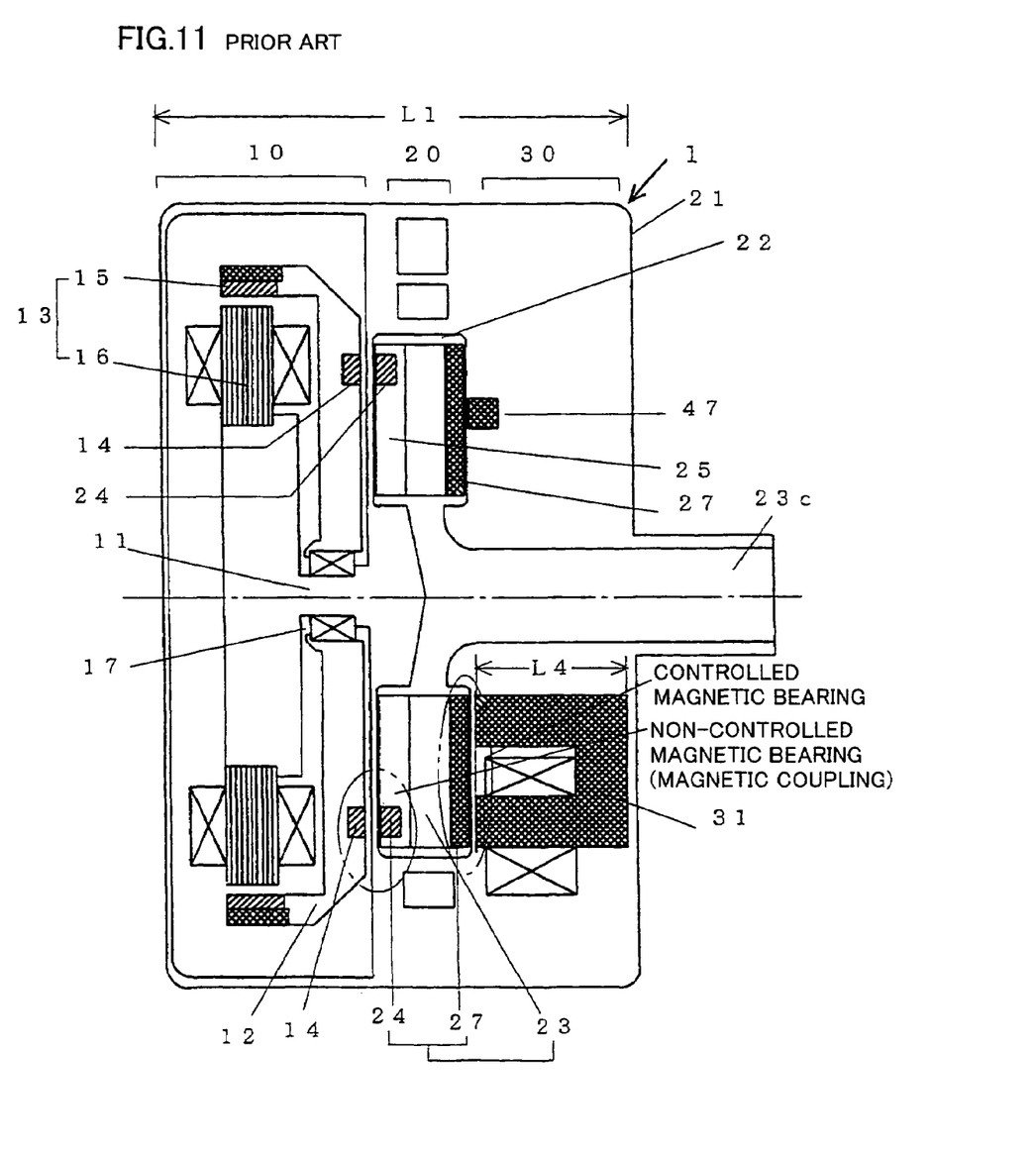
FIG. 11 shows a magnetically levitated pump of a first prior art example having an electro-magnet 31 for magnetic bearing and a motor 13 provided on opposite sides of an impeller 23.

FIG. 11 shows a magnetically levitated pump of a first prior art example having an electro-magnet 31 for magnetic bearing and a motor 13 provided on opposite sides of an impeller 23 (see FIG. 5 of Japanese Patent Laying-Open No. 2002-130177 and FIG. 16A of U.S. Pat. No. 6,626,644 B2). Referring to FIG. 11, the magnetically levitated pump of the first prior art example will be described. The magnetically levitated pump 1 of the first prior art example is formed of a motor unit 10, a pump unit 20 and a magnetic bearing unit 30. In a casing 21 of pump unit 20, a pump chamber 22 is provided. Impeller 23 rotates in this pump chamber 22. Impeller 23 has a plurality of blades, not shown.

Casing 21 is formed of a non-magnetic material, and impeller 23 is pivotally supported by a non-controlled magnetic bearing and a controlled magnetic bearing. The non-controlled magnetic bearing is formed of a rotor-side permanent magnet 14 and an impeller-side permanent magnet 24, while the controlled magnetic bearing is formed of an electro-magnet 31 for magnetic bearing and a soft magnetic member 27 opposite to the electro-magnet and to a position sensor. Impeller-side permanent magnet 24 is divided along the circumferential direction of impeller 23, and adjacent magnets are magnetized to have mutually opposite polarities.

Opposite to that side of impeller 23 which bears the impeller-side permanent magnet 24, a rotor 12 is provided pivotally supported by a fixed shaft 11, outside the pump chamber 22. Rotor 12 rotates, driven by motor 13. Rotor 12 has rotor-side permanent magnets 14 same in number as the impeller-side magnets, opposite to impeller-side permanent magnets 24 on impeller 23 and generating an attracting power.

In order to counterbalance the attractive force of rotor-side permanent magnets 14 and impeller-side permanent magnets 24 in the pump chamber 22 so that impeller 23 can be held at the center of pump chamber 22, three or more electro-magnets 31 for magnetic bearing and a position sensor 47 are provided on magnetic bearing unit 30. Electro-magnet 31 for magnetic bearing has a C-shape, and position sensor 47 is a magnetic sensor.

In magnetically levitated pump 1, attractive force in the axial direction acts between rotor-side permanent magnets 14 embedded in rotor 12 and impeller-side permanent magnets 24 provided on impeller 23. Magnetic coupling utilizing the attractive force is used for driving and rotating impeller 23 and for supporting impeller 23 in radial direction.

A current is caused to flow through a coil of electro-magnet 31 for magnetic bearing to counterbalance the attractive force, so that impeller 23 is lifted. When rotor 12 is rotated by the driving force of motor 13 including a motor rotor 15 and a motor stator 16, rotor-side permanent magnets 14 and impeller-side permanent magnets 24 form a magnetic coupling, whereby impeller 23 rotates, fluid is sucked in from an inlet port 23c, and emitted from an outlet port, not shown. Impeller 23 is isolated from rotor 12 by casing 21, and is free from any contamination from electro-magnets 31 for magnetic bearing, and therefore, the fluid (when applied as a blood pump, blood) emitted from magnetically levitated pump 1 is kept clean.

In this pump, however, electro-magnets 31 for magnetic bearing and motor 13 are provided on opposite sides of impeller 23, and therefore, axial length (hereinafter referred to as pump length L1) of the outer housing containing motor unit 10, pump unit 20 and magnetic bearing unit 30 becomes undesirably long. Japanese Patent Laying-Open No. 2002-130177 and U.S. Pat. No. 6,626,644 B2 also proposes a structure that addresses this problem. A second prior art example solving this problem will be described in the following.

[Second Prior Art Example (Description of FIG. 12)]

Figure 12:
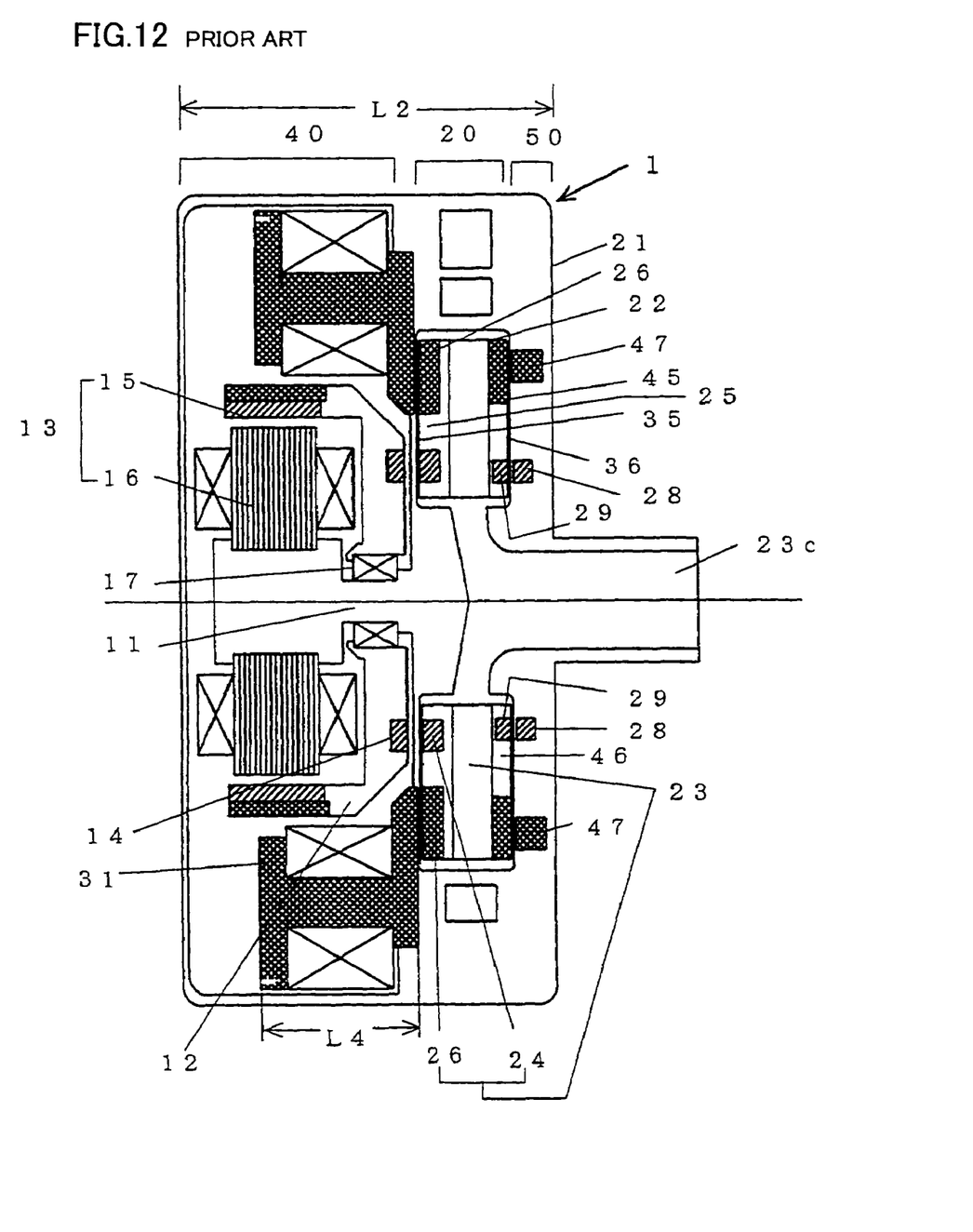
FIG. 12 shows a magnetically levitated pump of the second prior art example, having motor 13 and electro-magnets 31 for magnetic bearing arranged in a space on the same side.

FIG. 12 shows the magnetically levitated pump of the second prior art example, in which motor 13 and electro-magnets 31 for magnetic bearing are arranged in a space on the same side (see FIG. 3 of Japanese Patent Laying-Open No. 2002-130177 and FIG. 3 of U.S. Pat. No. 6,626,644 B2) Referring to FIG. 12, the magnetically levitated pump of the second prior art example will be described. Portions having the same functions as FIG. 11 are denoted by the same reference characters, and description thereof will not be repeated.

Different from the structure shown in FIG. 11, the magnetically levitated pump shown in FIG. 12 has motor 13 and electro-magnets 31 for magnetic bearing arranged in a space on the same side. Because of this structure, the axial length of the pump (hereinafter referred to as pump length L2) consisting of an actuator unit 40, pump unit 20 and casing unit 50 is made much shorter than pump length L1 of the first prior art example shown in FIG. 11.

The magnetically levitated pump shown in FIG. 12 includes an actuator unit 40, pump unit 20 and casing unit 50. Pump chamber 22 is provided in casing 21 of pump unit 20, and impeller 23 rotates in pump chamber 22.

Casing 21 is formed of plastic, ceramic, metal or the like. Of casing 21, an electro-magnets/impeller dividing wall 35 between actuator unit 40 and impeller 23, and a position sensor/impeller dividing wall 36 between position sensor 47 and impeller 23 cannot be formed of a magnetic material. Therefore, electro-magnets/impeller dividing wall 35 and position sensor/impeller dividing wall 36 are formed of a non-magnetic material.

Impeller 23 is supported by a non-controlled magnetic bearing and a controlled magnetic bearing. The non-controlled magnetic bearing is formed of an impeller-side permanent magnet 24 and rotor-side permanent magnets 14. Controlled magnetic bearing is formed of a soft magnetic member 26 opposite to the electro-magnets for magnetic bearing of impeller 23 and electro-magnets 31 for magnetic bearing.

In rotor-side non-magnetic material 25, impeller-side permanent magnet 24 and soft magnetic member 26 opposite to the electro-magnets for magnetic bearing are embedded. Impeller-side permanent magnet 24 is divided along the circumferential direction of impeller 23, and adjacent magnets are magnetized to have mutually opposite polarities.

Opposite to that side of impeller 23 which bears the impeller-side permanent magnet 24, a rotor 12 is provided pivotally supported by a fixed shaft 11, outside the pump chamber 22. Rotor 12 rotates, driven by motor 13. Rotor 12 has rotor-side permanent magnets 14 same in number as the impeller-side magnets, opposite to impeller-side permanent magnets 24 on impeller 23 and generating an attracting power.

Opposite to soft magnetic member 26 opposite to the electro-magnets for magnetic bearing of impeller 23, electro-magnets 31 for magnetic bearing are provided.

In a non-magnetic member 46 on the side of position sensor, a ring-shaped, impeller-side ferromagnetic body 29 and a soft magnetic member 45 opposite to position sensor are embedded. Opposite to soft magnetic member 45 of impeller 23, position sensor 47 is arranged, and opposite to impeller-side ferromagnetic body 29, a ring-shaped, casing-side permanent magnet 28 is arranged. The attractive force of impeller-side ferromagnetic body 29 and ring-shaped, casing-side permanent magnet 28 also attains support of impeller 23 in the radial direction.

Impeller 23 is movable in the axial direction in pump chamber 22, and materials and shapes of casing-side permanent magnet 28 and impeller-side ferromagnetic body 29 as well as the arrangement of casing-side permanent magnet 28 are determined so that the attractive force acting between casing-side permanent magnet 28 and impeller-side ferromagnetic body 29 is always larger than the attractive force acting on impeller-side permanent magnets 24 and rotor-side permanent magnets 14 within this movable range.

Using position sensor 47 and electro-magnets 31 for magnetic bearing, the attractive force acting between impeller-side permanent magnets 24 and rotor-side permanent magnets 14 is counterbalanced by the attractive force acting between impeller-side ferromagnetic body 29 and casing-side permanent magnet 28, whereby impeller 23 can be held at the center of pump chamber 22.

Magnetically levitated pump 1 shown in FIG. 11 has a problem that axial length of electro-magnets 31 for magnetic bearing in magnetic bearing unit 30 is long, and therefore pump length L1 including motor unit 10, pump unit 20 and magnetic bearing unit 30 becomes long.

In order to solve this problem, in the example of FIG. 12, magnetic bearing unit 30 and motor 13 are arranged in a space on the same side, so that the pump length including actuator unit 40, pump unit 20 and casing unit 50, that is, the pump length L2 along the axial direction mentioned above, is made shorter than pump length L1 of the first prior art example shown in FIG. 11, and the entire pump is made compact. When the magnetically levitated pump is to be used as an implanted blood pump, however, further size reduction of the pump is desirable.

SUMMARY OF THE INVENTION

A main object of the present invention is to provide a magnetically levitated pump that is made compact by (1) shortening axial length of the pump by arranging electro-magnets 31 for magnetic bearing and motor 13 in the same direction with respect to impeller 23, and by (2) reducing negative stiffness in the axial direction of impeller 23 generated by the mechanism for radially supporting impeller 23 realized by the attractive force of impeller-side ferromagnetic body 29 and ring-shaped, casing-side permanent magnet 28 having the structure shown in FIG. 12 of the second prior art example, to suppress maximum required attractive force f2 of electro-magnets 31 for magnetic bearing and thereby to make shorter the length L5 of the electro-magnets for magnetic bearing.

Figure 1:
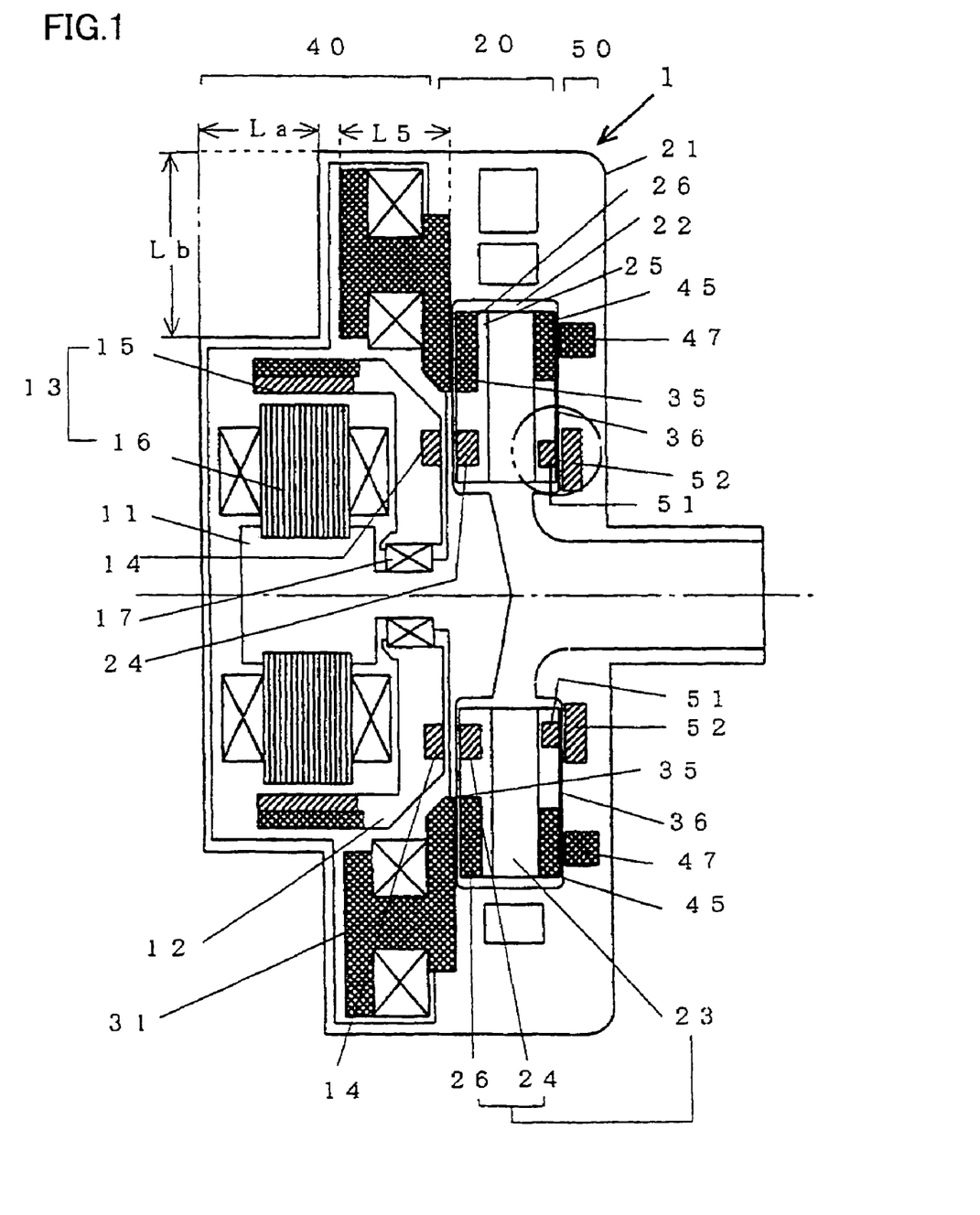
FIG. 1 shows a magnetically levitated pump 1 including a pump unit 20 and an actuator unit 40 having a motor rotor 15 and electro-magnets 31 for magnetic bearing arranged in the same direction to impeller 23, and a casing unit 50.

FIG. 1 shows a magnetically levitated pump 1 including: a pump unit 20 provided with a disk-shaped impeller 23 for feeding liquid; and an actuator unit 40 having a motor rotor 15 transmitting rotary driving force to pump unit 20 and electro-magnets 31 for magnetic bearing arranged in the same direction to impeller 23; wherein a current flowing through electro-magnets 31 for magnetic bearing is controlled to balance the attractive force between electro-magnets 31 for magnetic bearing and soft magnetic member 26 (first ferromagnetic body) opposite to the electro-magnets provided on one of the opposite surfaces of disk-shaped impeller 23 (hereinafter referred to as the actuator-facing impeller surface) opposite to electro-magnets 31 for magnetic bearing, the attractive force between an impeller-side ferromagnetic body 51 (second ferromagnetic body) provided on the other one of the opposite surfaces of disk-shaped impeller 23 that faces to casing unit 50 (hereinafter referred to as the casing-faced impeller surface) and a casing-side ferromagnetic body 52 (third ferromagnetic body) opposite to impeller-side ferromagnetic body 51 (second ferromagnetic body) and attracting impeller 23 toward the casing 50, the force acting on impeller generated by the rotary driving means (in FIG. 1, the attractive force between impeller-side permanent magnets 24 and rotor-side permanent magnets 14) and other disturbance influencing the impeller, so that the impeller is magnetically levitated; and surfaces of impeller-side ferromagnetic body 51 (second ferromagnetic body) and casing-side ferromagnetic body 52 (third ferromagnetic body) opposite to each other are adapted to have different shapes so that maximum required attractive force f2 of electro-magnets 31 for magnetic bearing is reduced, thereby enabling reduction in length L5 of the electro-magnets for the magnetic bearing.

As compared with the example of FIG. 12, in the magnetically levitated pump of the present invention shown in FIG. 1, opposite surfaces of impeller-side ferromagnetic body 51 (second ferromagnetic body) and casing-side ferromagnetic body 52 (third ferromagnetic body) have different shapes, so that the maximum required attractive force of electro-magnets 31 for magnetic bearing is reduced from f1 for the example of FIG. 12 to f2, whereby the length of the electro-magnets for the magnetic bearing is reduced from L4 of FIG. 12 to L5 of FIG. 1 and the magnetically levitated pump 1 is made compact.

The foregoing and other objects, features, aspects and advantages of the present invention will become more apparent from the following detailed description of the present invention when taken in conjunction with the accompanying drawings.

BRIEF DESCRIPTION OF THE DRAWINGS

(third ferromagnetic body), and the outer diameter of the second ferromagnetic body is made larger than the outer diameter of the third ferromagnetic body.

DESCRIPTION OF THE PREFERRED EMBODIMENTS

The invention according to the first embodiment is, as shown in FIG. 1, directed to a magnetically levitated pump 1 including: a pump unit 20 provided with a disk-shaped impeller 23 for feeding liquid; and an actuator unit 40 having a motor rotor 15 transmitting rotary driving force to impeller 23 and electro-magnets 31 for magnetic bearing exerting an attractive force on impeller 23, arranged in the same direction to impeller 23; wherein a soft magnetic member 26 (first ferromagnetic body) opposite to the electro-magnets is provided on the actuator-facing impeller surface, opposite to elector-magnets 31 for magnetic bearing;

an impeller-side ferromagnetic body 51 (second ferromagnetic body) is provided on the casing-faced impeller surface;

a casing-side ferromagnetic body 52 (third ferromagnetic body) is provided opposite to impeller-side ferromagnetic body 51 (second ferromagnetic body) for attracting impeller 23 toward the casing 50;

a current flowing through electro-magnets 31 for magnetic bearing is controlled to balance (1) "the attractive force between electro-magnets 31 for magnetic bearing and soft magnetic member 26 (first ferromagnetic body)", (2) "the attractive force between impeller-side ferromagnetic body 51 (second ferromagnetic body) and casing-side ferromagnetic body 52 (third ferromagnetic body)", (3) "the force acting on impeller 23 generated by the rotary driving means (in FIG. 1, the attractive force between impeller-side permanent magnets 24 and rotor-side permanent magnets 14)" and (4) "disturbances acting on impeller 23", so that the impeller is magnetically levitated; and wherein surfaces of impeller-side ferromagnetic body 51 (second ferromagnetic body) and casing-side ferromagnetic body 52 (third ferromagnetic body) opposite to each other are adapted to have different shapes so that maximum required attractive force f2 of electro-magnets 31 for magnetic bearing is reduced, thereby enabling reduction in length L5 of the electro-magnets for the magnetic bearing.

The invention according to the second embodiment is, as shown in FIGS. 3 to 10, directed to the magnetically levitated pump of the first embodiment, wherein impeller-side ferromagnetic body 51 (second ferromagnetic body) or casing-side ferromagnetic body 52 (third ferromagnetic body) has a ring-shape.

The invention according to the third embodiment is, as shown in FIGS. 7 to 10, directed to the magnetically levitated pump of the first or second embodiment, wherein impeller-side ferromagnetic body 51 (second ferromagnetic body) or casing-side ferromagnetic body 52 (third ferromagnetic body) is formed of a plurality of ferromagnetic bodies arranged in the circumferential direction.

The invention according to the fourth embodiment is, as shown in FIG. 3 or 5 or FIGS. 7 to 10, directed to the magnetically levitated pump of the first to third embodiments, wherein the diameter of an approximated inscribed circle of impeller-side ferromagnetic body 51 (second ferromagnetic body) is made larger than the diameter of an approximated inscribed circle of casing-side ferromagnetic body 52 (third ferromagnetic body).

Figure 4:
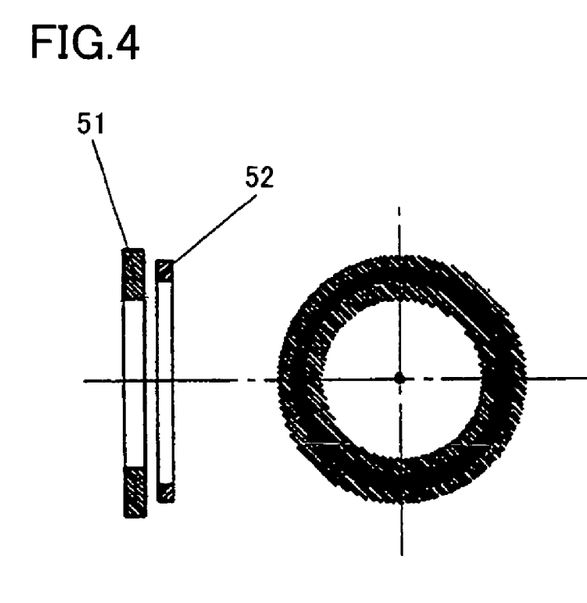
FIG. 4 is an illustration showing ferromagnetic bodies having opposite surfaces of different shapes, that is, the inner diameter of ring-shaped impeller-side ferromagnetic body 51 (second ferromagnetic body) is made smaller than the inner diameter of ring-shaped casing-side ferromagnetic body 52
Figure 6:
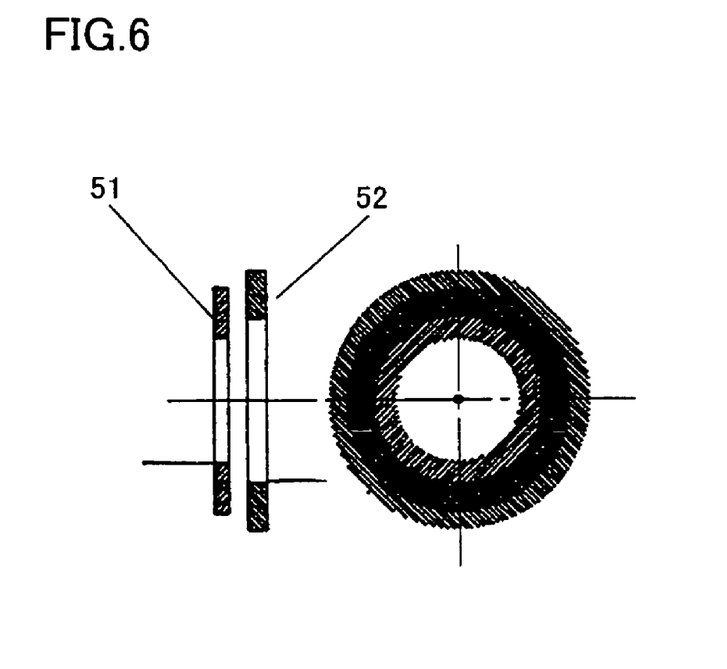
FIG. 6 is an illustration showing ferromagnetic bodies having opposite surfaces of different shapes, that is, the inner and outer diameters of ring-shaped impeller-side ferromagnetic body 51 (second ferromagnetic body) are made smaller than the inner and outer diameters of casing-side ferromagnetic body 52 (third ferromagnetic body), respectively.

The invention according to the fifth embodiment is, as shown in FIG. 4 or 6, directed to the magnetically levitated pump of the first to third embodiments, wherein the diameter of an approximated inscribed circle of impeller-side ferromagnetic body 51 (second ferromagnetic body) is made smaller than the diameter of an approximated inscribed circle of casing-side ferromagnetic body 52 (third ferromagnetic body).

Figure 5:
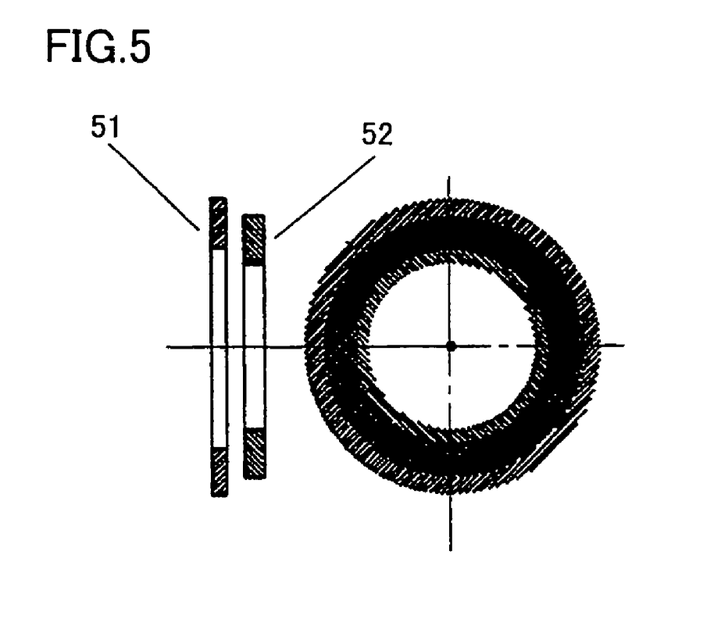
FIG. 5 is an illustration showing ferromagnetic bodies having opposite surfaces of different shapes, that is, the inner and outer diameters of ring-shaped impeller-side ferromagnetic body 51 (second ferromagnetic body) are made larger than the inner and outer diameters of casing-side ferromagnetic body 52 (third ferromagnetic body), respectively.

The invention according to the sixth embodiment is, as shown in FIG. 4 or 5, directed to the magnetically levitated pump of the first to third embodiments, wherein the diameter of an approximated circumscribed circle of impeller-side ferromagnetic body 51 (second ferromagnetic body) is made larger than the diameter of an approximated circumscribed circle of casing-side ferromagnetic body 52 (third ferromagnetic body).

The invention according to the seventh embodiment is, as shown in FIG. 3 or FIGS. 6 to 10, directed to the magnetically levitated pump of the first to third embodiments, wherein the diameter of an approximated circumscribed circle of impeller-side ferromagnetic body 51 (second ferromagnetic body)

is made smaller than the diameter of an approximated circumscribed circle of casing-side ferromagnetic body 52 (third ferromagnetic body).

The invention according to the eighth embodiment is directed to the magnetically levitated pump of the first to seventh embodiments, wherein impeller-side ferromagnetic body 51 (second ferromagnetic body) is a permanent magnet, or casing-side ferromagnetic body 52 (third ferromagnetic body) is a permanent magnet.

Figure 13:
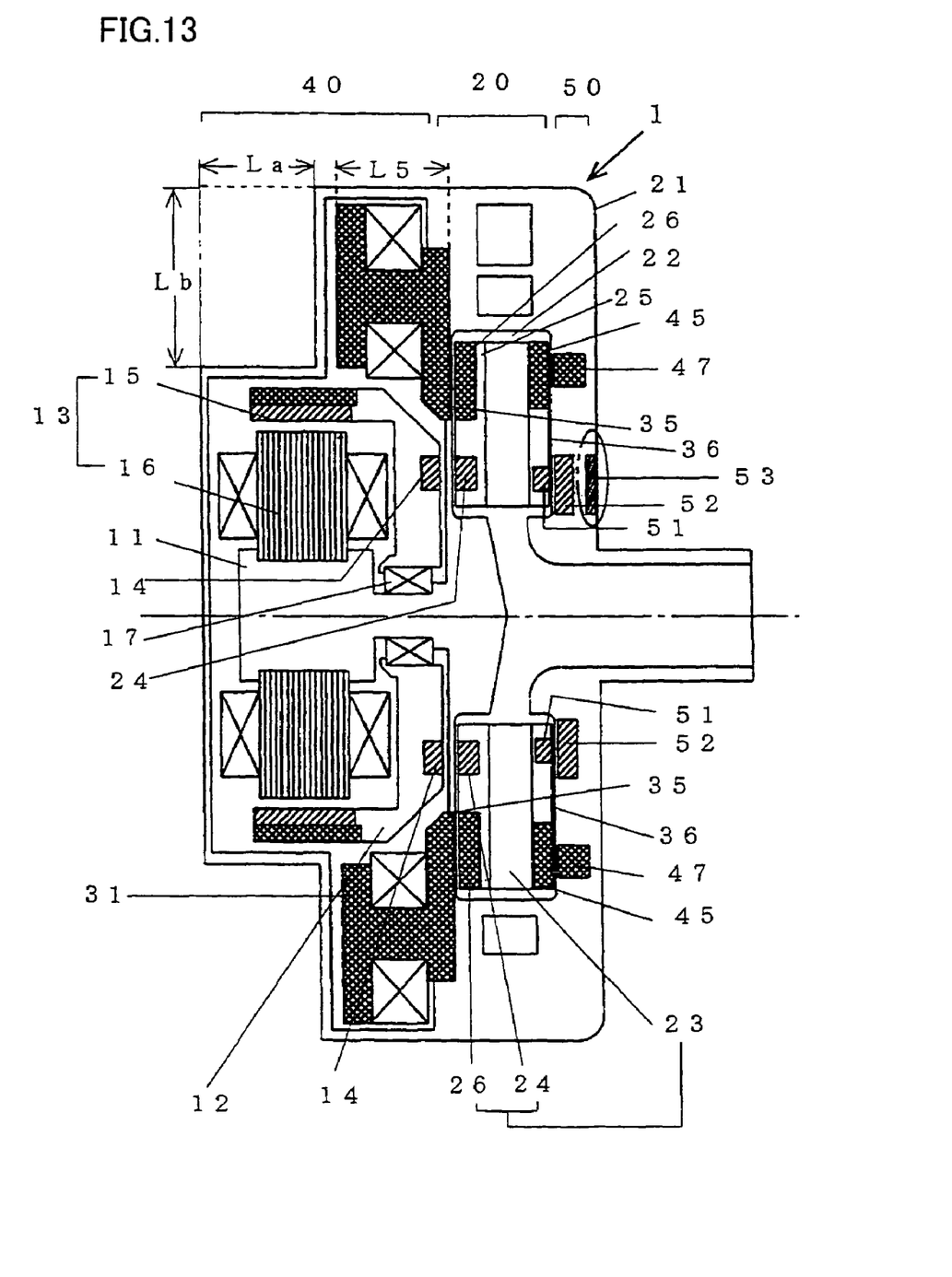
FIG. 13 shows a magnetically levitated pump with a leakage flux shielding structure in which a ferromagnetic body 53 (fourth ferromagnetic body) is arranged on that side of casing-side ferromagnetic body 52 which does not face to impeller 23.

The invention according to the ninth embodiment is, as shown in FIG. 13, directed to the magnetically levitated pump of the first to eighth embodiments, wherein a ferromagnetic body 53 (fourth ferromagnetic body) is arranged on that side of casing-side ferromagnetic body 52 (third ferromagnetic body) which does not face to impeller 23, so as to suppress leakage flux to the outside of the pump.

The invention according to the tenth embodiment is, as shown in FIG. 1, directed to the magnetically levitated pump of the first to ninth embodiments, wherein the rotor-side permanent magnet 14 (first permanent magnet) is arranged on that surface of rotor 12 which faces impeller 23, and the impeller-side permanent magnet 24 (second permanent magnet) is arranged opposite thereto on the surface of impeller 23, whereby a magnetic coupling is formed by rotor-side permanent magnet 14 and impeller-side permanent magnet 24, rotor 12 is rotated and impeller 23 is driven and rotated.

The invention according to the eleventh embodiment is directed to the magnetically levitated pump of the first to tenth embodiments, used as a blood pump.

EMBODIMENTS

[The Present Invention (Description of FIG. 1)]

FIG. 1 shows a magnetically levitated pump in which, similar to the second prior art example, motor 13 and electro-magnets 31 for magnetic bearing are arranged in a space on the same side. Referring to FIG. 1, the magnetically levitated pump of the present invention will be described. Functions similar to those of FIG. 12 are denoted by the same reference characters, and description thereof will not be repeated.

Similar to the second prior art example described with reference to FIG. 12 above, magnetically levitated pump 1 of the present invention shown in FIG. 1 includes: a pump unit 20 provided with a disk-shaped impeller 23 for feeding liquid; an actuator unit 40 having a motor 13 for rotating impeller 23 and electro-magnets 31 for magnetic bearing exerting an attractive force on impeller 23, arranged in the same direction to impeller 23; and a casing unit 50 having a position sensor 47 arranged thereon, for measuring levitation position of impeller 23.

In magnetically levitated pump 1 of the present invention having such a structure, a current flowing through electro-magnets 31 for magnetic bearing is controlled to balance the attractive force between electro-magnets 31 for magnetic bearing and soft magnetic member 26 (first ferromagnetic body) opposite to the electro-magnets provided on the actuator-facing impeller surface opposite to electro-magnets 31 for magnetic bearing, the attractive force between an impeller-side ferromagnetic body 51 (second ferromagnetic body) provided on the casing-faced impeller surface and a casing-side ferromagnetic body 52 (third ferromagnetic body) opposite to impeller-side ferromagnetic body 51 (second ferromagnetic body) and attracting impeller 23 toward the casing 50, the force acting on impeller generated by the rotary driving means (in FIG. 1, the attractive force between impeller-side permanent magnets 24 and rotor-side permanent magnets 14) and disturbance influencing the impeller, so that the impeller is magnetically levitated.

Different from the first and second prior art examples, in magnetically levitated pump 1 of the present invention, opposite surfaces of impeller-side ferromagnetic body 51 (second ferromagnetic body) and casing-side ferromagnetic body 52 (third ferromagnetic body) have different shapes, so that the maximum required attractive force of electro-magnets 31 for magnetic bearing is reduced from f1 of the second prior art example to f2, whereby the length of the electro-magnets of the magnetic bearing is reduced from L4 of the second prior art example to L5, and as a result, the magnetically levitated pump can be made compact by a volume corresponding to a cylindrical body of La×Lb, that is the product of axial length La of pump outer housing and reduction width Lb in diametral direction of pump outer housing.

Figure 2A:
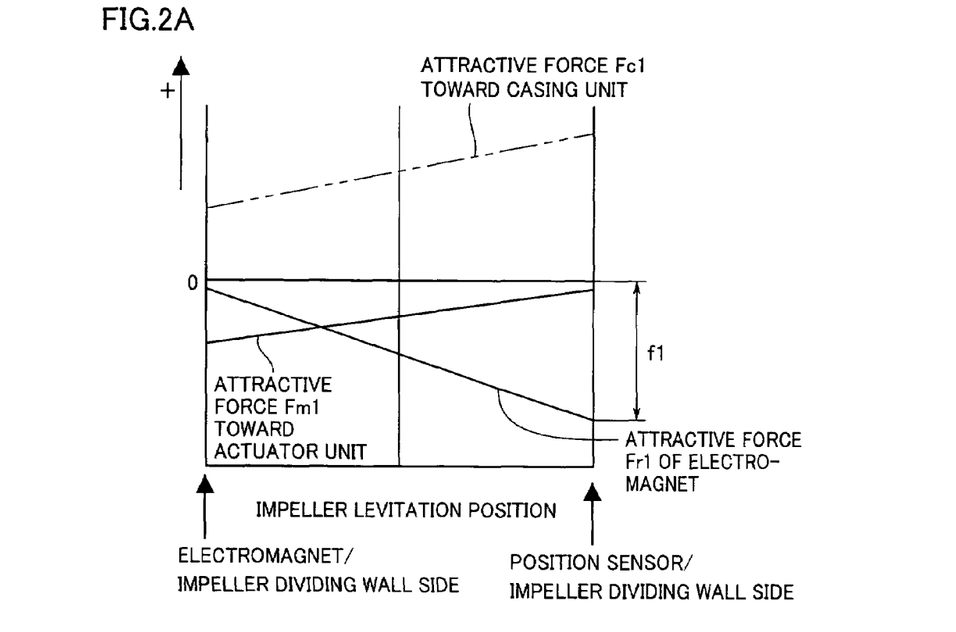
FIG. 2A is a first characteristic diagram of impeller levitation position and impeller force, representing a relation between the position of impeller levitation in pump chamber 22 (abscissa) and the force acting on impeller 23 (ordinate).
Figure 2B:
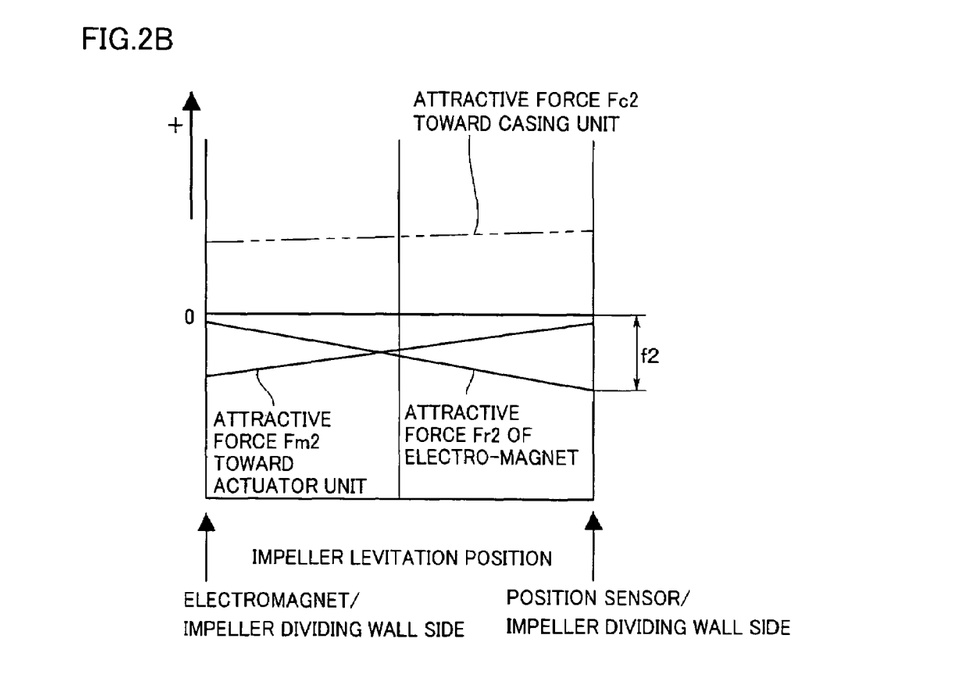
FIG. 2B is a second characteristic diagram of impeller levitation position and impeller force, representing a relation between the position of impeller levitation in pump chamber 22 (abscissa) and the force acting on impeller 23 (ordinate).

[Description of FIGS. 2A and 2B]

FIGS. 2A and 2B are characteristic diagrams of impeller levitation position and impeller force, representing a relation between the position of impeller levitation from electro-magnets/impeller dividing wall 35 and position sensor/impeller dividing wall 36 in pump chamber 22 (abscissa) and the force acting on impeller 23 (ordinate). FIG. 2A is a characteristic diagram of impeller levitation position and impeller force of the conventional structure shown in FIG. 12, and FIG. 2B is a characteristic diagram of impeller levitation position and impeller force of the structure of the present invention shown in FIG. 1. Both figures represent a state in which the attractive forces Fm1 and Fm2 to the direction of the actuator generated between impeller-side permanent magnets 24 and rotor-side permanent magnets 14 are the same.

The abscissa represents the distance from electro-magnets/impeller dividing wall 35 to impeller 23, in pump chamber 22. The ordinate represents the force acting on impeller 23. In the figure, as the forces acting on impeller 23, (1) attractive force Fc to the casing side generated between impeller-side ferromagnetic body 51 (second ferromagnetic body) and the casing-side ferromagnetic body 52 (third ferromagnetic body) and (2) attractive force Fm to the actuator side generated between impeller-side permanent magnets 24 and rotor-side permanent magnets 14 are denoted. Further, an electro-magnet attractive force Fr required between electro-magnets 31 for magnetic bearing and soft magnetic member 26 opposite to the electro-magnets for levitating impeller 23 to the levitation position against the above-identified attractive forces is calculated by adding the attractive force Fc to the casing side and attractive force Fm to the actuator side, and denoted. In FIGS. 2A and 2B, the attractive force by which impeller 23 is attracted to the side of casing is indicated as (+) along the ordinate, and it is assumed that there is no other disturbance affecting the impeller 23.

In the following, the characteristic diagram of impeller levitation position and impeller force of the conventional structure of FIG. 2A will be compared with the characteristic diagram of impeller levitation position and impeller force of the structure in accordance with the present invention shown in FIG. 2B.

The movable range of impeller 23 in pump chamber 22 is limited by electro-magnets/impeller dividing wall 35 and position sensor/impeller dividing wall 36. An electro-magnet can generate only the attractive force and not the repulsive force. Therefore, in both structures shown in FIGS. 12 and 1, in order to control the levitation position of impeller 23 by electro-magnets 31 for magnetic bearing, it is always necessary that |attractive force Fc to the casing side|>|attractive force Fm to the actuator side|, in the movable range of impeller 23 in pump chamber 22.

As shown in FIG. 2B, by making difference between the shapes of opposite surfaces of impeller-side ferromagnetic body 51 (second ferromagnetic body) and casing-side ferromagnetic body (third ferromagnetic body) opposite thereto, the amount of increase/decrease of the attractive force Fc to the casing side caused by the positional change of impeller 23 can be made smaller, and therefore, the change in attractive force Fr of electro-magnets 31 for magnetic bearing can also be made smaller then in the case of FIG. 2A, by the position of the impeller. Therefore, maximum required attractive force of electro-magnets 31 for magnetic bearing can be made smaller than the maximum required attractive force f1 shown in FIG. 2A. As the maximum required attractive force of electro-magnets 31 for magnetic bearing can be reduced, it becomes possible to reduce the attractive force of electro-magnets 31 for magnetic bearing, it becomes possible to reduce the number of coil windings inside and to make shorter the length of electro-magnets 31 for magnetic bearing. As a result, in FIG. 1, the number of coil windings around electro-magnets 31 for magnetic bearing can be reduced from that of FIG. 12, and hence, electro-magnets 31 for magnetic bearing and the pump itself can be made compact.

As shown in FIG. 2B, other possible methods of reducing the attractive force Fc to the casing side generated between impeller-side ferromagnetic body 51 (second ferromagnetic body) and the casing-side ferromagnetic body 52 (third ferromagnetic body) may include (1) the method in which the impeller-side ferromagnetic body 51 (second ferromagnetic body) is made thicker and the casing-side ferromagnetic body 52 (third ferromagnetic body) is placed away from the impeller-side ferromagnetic body 51 (second ferromagnetic body), and (2) the method in which the thickness of the impeller-side ferromagnetic body 51 (second ferromagnetic body) is kept unchanged, and the casing-side ferromagnetic body 52 (third ferromagnetic body) is made thicker and placed away from the impeller-side ferromagnetic body 51 (second ferromagnetic body). Both of these methods are undesirable in view of reduction in size of the pump, as the length of the pump in the axial direction (left/right direction in the figure) increases in both methods.

In FIG. 1, position sensor 47 is arranged on casing unit 50. The sensor may be arranged on the same side and near electro-magnets 31 for magnetic bearing, as in the first prior art example shown in FIG. 11. Further, though a magnetic coupling is provided for rotationally driving impeller 23 in FIG. 1, a method may be adopted in which the impeller is rotationally driven by electrically providing a rotational magnetic field on the impeller-side permanent magnets 24.

[Description of FIGS. 3 to 10]

FIGS. 3 to 10 represent embodiments of the present invention related to the arrangement and shapes of impeller-side ferromagnetic body 51 (second ferromagnetic body) and casing-side ferromagnetic body 52 (third ferromagnetic body). In these figures, only the relations and shapes of these two ferromagnetic bodies are shown, and other components, structures and the like of the pump are not addressed. Further, in these figures, perspective views along the axial direction are shown on the right side.

Figure 3:
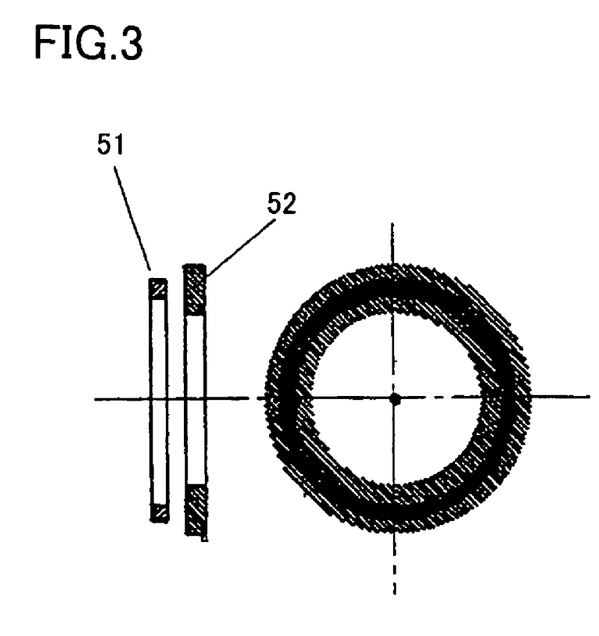
FIG. 3 is an illustration showing ferromagnetic bodies having opposite surfaces of different shapes, that is, the inner diameter of ring-shaped impeller-side ferromagnetic body 51 (second ferromagnetic body) is made larger than the inner diameter of ring-shaped casing-side ferromagnetic body 52 (third ferromagnetic body), and the outer diameter of the second ferromagnetic body is made smaller than the outer diameter of the third ferromagnetic body.

FIG. 3 shows ferromagnetic bodies having opposite surfaces of different shapes, in which both ferromagnetic bodies have a ring-shape, and the inner diameter of impeller-side ferromagnetic body 51 (second ferromagnetic body) is made larger than the inner diameter of casing-side ferromagnetic body 52 (third ferromagnetic body), and the outer diameter of impeller-side ferromagnetic body 51 (second ferromagnetic body) is made smaller than the inner diameter of casing-side ferromagnetic body 52 (third ferromagnetic body). Though the two ferromagnetic bodies are adapted to have different inner and outer diameters in this example, one of the inner and outer diameters may be the same. Further, the materials of the two ferromagnetic bodies may be selected such that the attractive force acts in mutually opposite directions, and one or both of the ferromagnetic bodies may be formed of a permanent magnet.

FIG. 4 shows ferromagnetic bodies having opposite surfaces of different shapes, in which both ferromagnetic bodies have a ring-shape, and the inner diameter of impeller-side ferromagnetic body 51 (second ferromagnetic body) is made smaller than the inner diameter of casing-side ferromagnetic body 52 (third ferromagnetic body), and the outer diameter of impeller-side ferromagnetic body 51 (second ferromagnetic body) is made larger than the inner diameter of casing-side ferromagnetic body 52 (third ferromagnetic body). Though the two ferromagnetic bodies are adapted to have different inner and outer diameters in this example, one of the inner and outer diameters may be the same. Further, the materials of the two ferromagnetic bodies may be selected such that the attractive force acts in mutually opposite directions, and one or both of the ferromagnetic bodies may be formed of a permanent magnet.

FIG. 5 shows ferromagnetic bodies having opposite surfaces of different shapes, in which both ferromagnetic bodies have a ring-shape, and the inner and outer diameters of impeller-side ferromagnetic body 51 (second ferromagnetic body) are made larger than the inner and outer diameters of casing-side ferromagnetic body 52 (third ferromagnetic body), respectively. Though the two ferromagnetic bodies are adapted to have different inner and outer diameters in this example, one of the diameters may be the same. Further, the materials of the two ferromagnetic bodies may be selected such that the attractive force acts in mutually opposite directions, and one or both of the ferromagnetic bodies may be formed of a permanent magnet.

FIG. 6 shows ferromagnetic bodies having opposite surfaces of different shapes, in which both ferromagnetic bodies have a ring-shape, and the inner and outer diameters of impeller-side ferromagnetic body 51 (second ferromagnetic body) are made smaller than the inner and outer diameters of casing-side ferromagnetic body 52 (third ferromagnetic body), respectively. Though the two ferromagnetic bodies are adapted to have different inner and outer diameters in this example, one of the diameters may be the same. Further, the materials of the two ferromagnetic bodies may be selected such that the attractive force acts in mutually opposite directions, and one or both of the ferromagnetic bodies may be formed of a permanent magnet.

Figure 7:
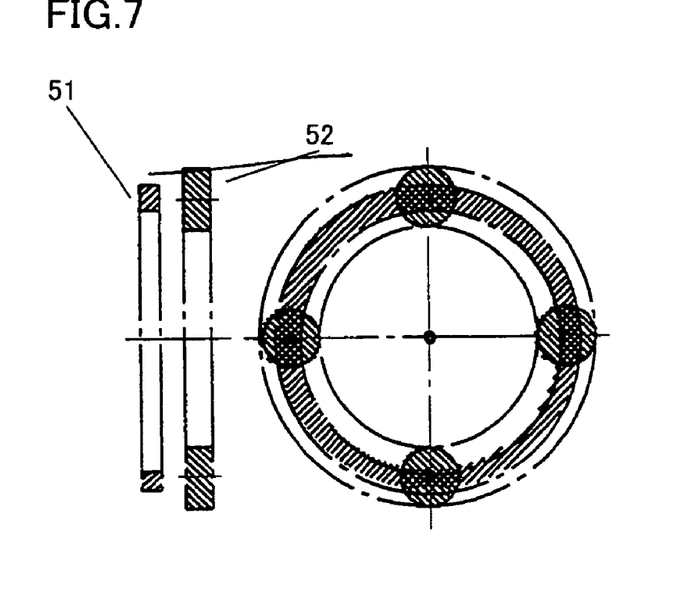
FIG. 7 is an illustration showing ferromagnetic-bodies having opposite surfaces of different shapes, that is, impeller-side ferromagnetic body 51 (second ferromagnetic body) has a ring-shape, and casing-side ferromagnetic body 52 (third ferromagnetic body) is formed of four bar-magnets all magnetized in the same direction.

FIG. 7 shows ferromagnetic bodies having opposite surfaces of different shapes, in which impeller-side ferromagnetic body 51 (second ferromagnetic body) has a ring-shape, and casing-side ferromagnetic body 52 (third ferromagnetic body) is formed of four bar-magnets all magnetized in the same direction. Further, the diameter of an inscribed circle of casing-side ferromagnetic body 52 (third ferromagnetic body) is smaller than the inner diameter of impeller-side ferromagnetic body 51 (second ferromagnetic body), and the diameter of a circumscribed circle of casing-side ferromagnetic body 52 (third ferromagnetic body) is larger than the outer diameter of impeller-side ferromagnetic body 51 (second ferromagnetic body).

Though the inner diameter and the diameter of the inscribed circle, and the outer diameter and the diameter of the circumscribed circle of the two ferromagnetic bodies are made different from each other in this example, one of these may be the same. Though the ferromagnetic body is implemented by four bar-magnets here, the number thereof is not limited. Further, casing-side ferromagnetic body 52 (third ferromagnetic body) may be a soft magnetic member. The materials of impeller-side ferromagnetic body 51 and casing-side ferromagnetic body 52 may be selected such that the attractive force acts in mutually opposite directions, and both may be permanent magnets, or impeller-side ferromagnetic body 51 may be formed of a permanent magnet and casing-side ferromagnetic body 52 may be formed of a soft magnetic body.

Figure 8:
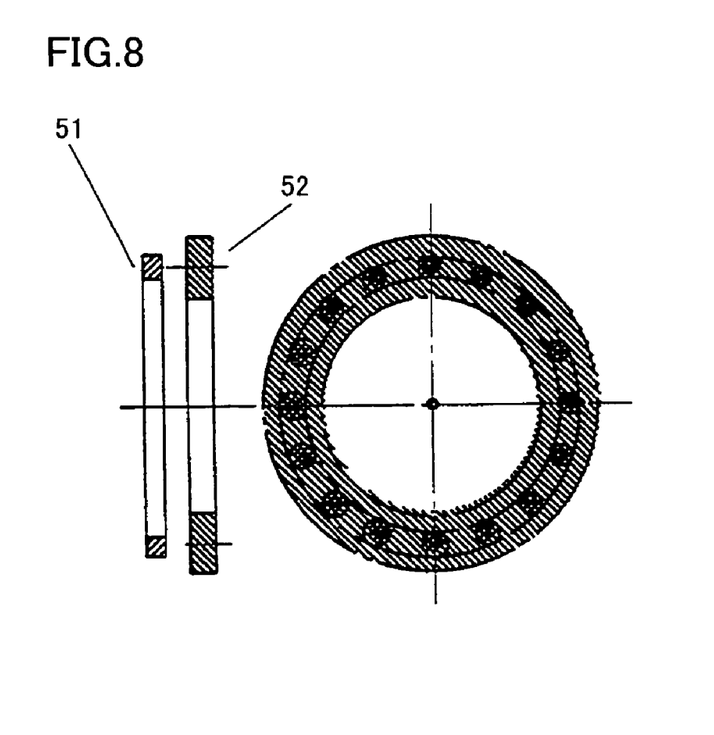
FIG. 8 is an illustration showing ferromagnetic bodies having opposite surfaces of different shapes, that is, casing-side ferromagnetic body 52 (third ferromagnetic body) has a ring-shape, and impeller-side ferromagnetic body 51 (second ferromagnetic body) is formed of sixteen bar-magnets all magnetized in the same direction.

FIG. 8 shows ferromagnetic bodies having opposite surfaces of different shapes, in which casing-side ferromagnetic body 52 (third ferromagnetic body) has a ring-shape, and impeller-side ferromagnetic body 51 (second ferromagnetic body) is formed of sixteen bar-magnets all magnetized in the same direction. Further, the diameter of an inscribed circle of impeller-side ferromagnetic body 51 (second ferromagnetic body) is made larger than the inner diameter of casing-side ferromagnetic body 52 (third ferromagnetic body), and the diameter of a circumscribed circle of impeller-side ferromagnetic body 51 (second ferromagnetic body) is made smaller than the outer diameter of casing-side ferromagnetic body 52 (third ferromagnetic body).

Though the inner diameter and the diameter of the inscribed circle, and the outer diameter and the diameter of the circumscribed circle of the two ferromagnetic bodies are made different from each other in this example, one of these may be the same. Though the ferromagnetic body is implemented by sixteen bar-magnets here, the number thereof is not limited. Further, casing-side ferromagnetic body 52 (third ferromagnetic body) may be a soft magnetic member. The materials of impeller-side ferromagnetic body 51 and casing-side ferromagnetic body 52 may be selected such that the attractive force acts in mutually opposite directions, and both may be permanent magnets, or impeller-side ferromagnetic body 51 may be formed of a permanent magnet and casing-side ferromagnetic body 52 may be formed of a soft magnetic body.

Figure 9:
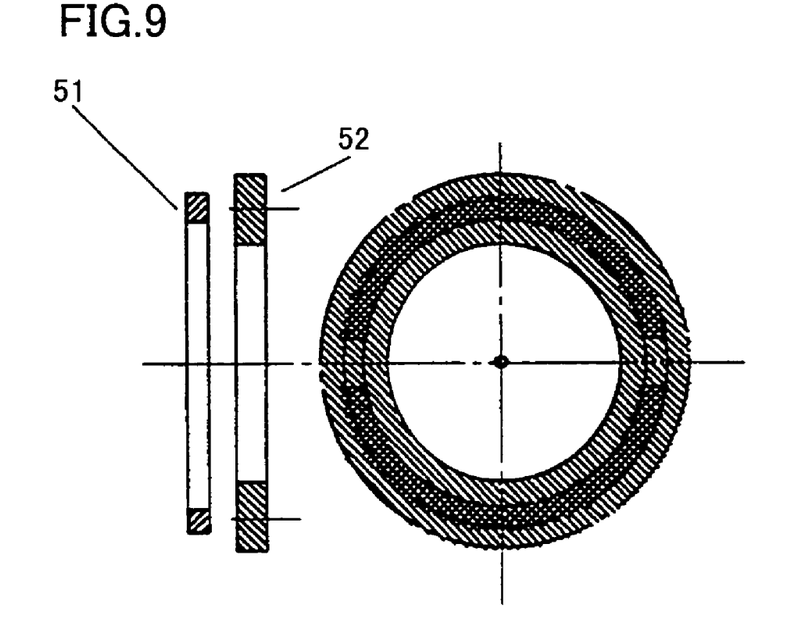
FIG. 9 is an illustration showing ferromagnetic bodies having opposite surfaces of different shapes, that is, casing-side ferromagnetic body 52 (third ferromagnetic body) has a ring-shape, and impeller-side ferromagnetic body 51 (second ferromagnetic body) is formed of two plate-magnets magnetized in the same direction.

FIG. 9 shows ferromagnetic bodies having opposite surfaces of different shapes, in which casing-side ferromagnetic body 52 (third ferromagnetic body) has a ring-shape, and impeller-side ferromagnetic body 51 (second ferromagnetic body) is formed of two plate-magnets magnetized in the same direction.

Though the inner diameter and the diameter of the inscribed circle, and the outer diameter and the diameter of the circumscribed circle of the two ferromagnetic bodies are made different from each other in this example, one of these may be the same. Though the impeller-side ferromagnetic body 51 is implemented by two plate-shaped magnets here, the number thereof is not limited. Further, casing-side ferromagnetic body 52 (third ferromagnetic body) may be a soft magnetic member. The materials of impeller-side ferromagnetic body 51 and casing-side ferromagnetic body 52 may be selected such that the attractive force acts in mutually opposite directions, and both may be permanent magnets, or impeller-side ferromagnetic body 51 may be formed of a permanent magnet and casing-side ferromagnetic body 52 may be formed of a soft magnetic body.

Figure 10:
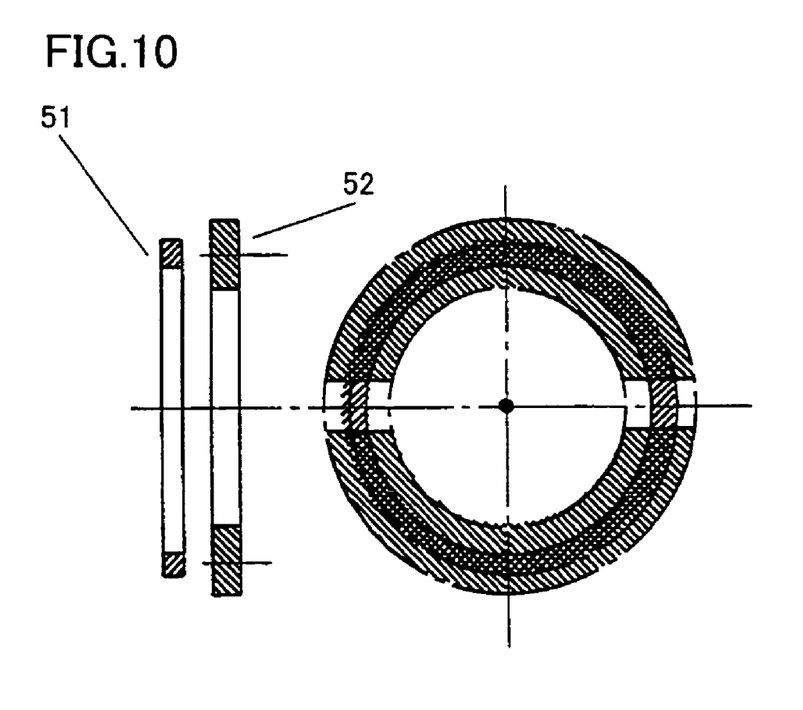
FIG. 10 is an illustration showing ferromagnetic bodies having opposite surfaces of different shapes, that is, impeller-side ferromagnetic body 51 (second ferromagnetic body) has a ring-shape, and casing-side ferromagnetic body 52 (third ferromagnetic body) is formed of two plate-magnets magnetized in the same direction.

FIG. 10 shows ferromagnetic bodies having opposite surfaces of different shapes, in which impeller-side ferromagnetic body 51 (second ferromagnetic body) has a ring-shape, and casing-side ferromagnetic body 52 (third ferromagnetic body) is formed of two plate-magnets magnetized in the same direction.

Though the inner diameter and the diameter of the inscribed circle, and the outer diameter and the diameter of the circumscribed circle of the two ferromagnetic bodies are made different from each other in this example, one of these may be the same. Though the casing-side ferromagnetic body 52 is implemented by two plate-shaped magnets here, the number thereof is not limited. The materials of impeller-side ferromagnetic body 51 and casing-side ferromagnetic body 52 may be selected such that the attractive force acts in mutually opposite directions, and both may be permanent magnets, or impeller-side ferromagnetic body 51 may be formed of a permanent magnet and casing-side ferromagnetic body 52 may be formed of a soft magnetic body.

FIG. 13 shows a magnetically levitated pump with a leakage flux shielding structure preventing leakage to the outside of pump 1, in which a ferromagnetic body 53 (fourth ferromagnetic body) is arranged on that side of casing-side ferromagnetic body 52 which does not face to impeller 23. Different from FIG. 1, in this example, ferromagnetic body 53 (fourth ferromagnetic body) is placed, so that leakage flux from casing-side ferromagnetic body 52 to the outside of pump 1 can be shielded, and any flux from the outside of pump 1 can also be shielded, so that stable lifting of impeller 23 is ensured. Here, ferromagnetic body 53 (fourth ferromagnetic body) may be of a soft magnetic material or a hard magnetic material.

Though position sensor 47 is arranged near casing-side ferromagnetic body 52 in the pump structure shown in FIG. 1, it may be arranged in actuator unit 40.

According to the present invention, a current flowing through electro-magnets 31 for magnetic bearing is controlled to balance (1) the attractive force between electro-magnets 31 for magnetic bearing and soft magnetic member 26 (first ferromagnetic body) opposite to the electro-magnets provided on the actuator-facing impeller surface opposite to electro-magnets 31 for magnetic bearing, (2) the attractive force between impeller-side ferromagnetic body 51 (second ferromagnetic body) provided on the casing-faced impeller surface and casing-side ferromagnetic body 52 (third ferromagnetic body) opposite to impeller-side ferromagnetic body 51 (second ferromagnetic body) and attracting impeller 23 toward the casing 50, (3) the force acting on impeller generated by the rotary driving means (in FIG. 1, the attractive force between impeller-side permanent magnets 24 and rotor-side permanent magnets 14) and (4) other disturbance influencing the impeller, so that the impeller is magnetically levitated; and surfaces of impeller-side ferromagnetic body 51 (second ferromagnetic body) and casing-side ferromagnetic body 52 (third ferromagnetic body) opposite to each other are adapted to have different shapes so that maximum required attractive force f2 of electro-magnets 31 for magnetic bearing is reduced, thereby enabling reduction in length L5 of the electro-magnets for the magnetic bearing.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A magnetically levitated pump, comprising:
   a pump unit including a disk-shaped impeller for feeding liquid;
   a magnetic bearing unit provided opposite to one of end faces along an axial direction of said impeller; and a casing unit provided opposite to the other of said end faces;
wherein said magnetic bearing unit includes:
rotary driving means for transmitting a rotational driving force to said impeller, and
an electro-magnet for a magnetic bearing;
said pump unit includes:
a soft magnetic member opposite to the electro-magnet provided on said one of said end faces of said impeller and provided opposite to said electro-magnet for magnetic bearing, and
an impeller-side ferromagnetic body provided on said other of said end faces of said impeller;
said casing unit includes a casing-side ferromagnetic body provided opposite to said impeller-side ferromagnetic body and attracting said impeller toward said casing unit;
said electro-magnet for the magnetic bearing has a magnetizing current flowing therethrough controlled to balance an attractive force between said electro-magnet for the magnetic bearing and said soft magnetic member opposite to the electro-magnet, an attractive force between said impeller-side ferromagnetic body and said casing-side ferromagnetic body, a force acting on said impeller generated by said rotary driving means, and other disturbance influencing said impeller; and
opposite surfaces of said impeller-side ferromagnetic body and said casing-side ferromagnetic body are adapted to have mutually different shapes from each other, so that a maximum required attractive force is suppressed between said electro-magnet for the magnetic bearing and said soft magnetic member opposite to the electro-magnet.

2. The magnetically levitated pump according to claim 1, wherein said impeller-side ferromagnetic body or said casing-side ferromagnetic body has a ring-shape.

3. The magnetically levitated pump according to claim 1 wherein said impeller-side ferromagnetic body or said casing-side ferromagnetic body is formed of a plurality of ferromagnetic bodies arranged in a circumferential direction.

4. The magnetically levitated pump according to claim 1, wherein diameter of an approximated inscribed circle of said impeller-side ferromagnetic body is larger than diameter of an approximated inscribed circle of said casing-side ferromagnetic body.

5. The magnetically levitated pump according to claim 1, wherein diameter of an approximated inscribed circle of said impeller-side ferromagnetic body is smaller than diameter of an approximated inscribed circle of said casing-side ferromagnetic body.

6. The magnetically levitated pump according to claim 1, wherein diameter of an approximated circumscribed circle of said impeller-side ferromagnetic body is larger than diameter of an approximated circumscribed circle of said casing-side ferromagnetic body.

7. The magnetically levitated pump according to claim 1, wherein diameter of an approximated circumscribed circle of said impeller-side ferromagnetic body is smaller than diameter of an approximated circumscribed circle of said casing-side ferromagnetic body.

8. The magnetically levitated pump according to claim 1, wherein said impeller-side ferromagnetic body or said casing-side ferromagnetic body is formed of a permanent magnet.

9. The magnetically levitated pump according to claim 1, wherein said casing unit further includes a ferromagnetic body arranged on that side of casing-side ferromagnetic body which does not face to said impeller.

10. The magnetically levitated pump according to claim 1, wherein said rotary driving means includes a rotor provided opposite to said impeller,
said impeller has an impeller-side permanent magnet arranged on said one of said end faces,
said rotor has a rotor-side permanent magnet arranged opposite to said impeller-side permanent magnet,
said rotary driving means rotationally drives said impeller by a magnetic coupling formed between said impeller-side permanent magnet and said rotor-side permanent magnet.

11. The magnetically levitated pump according to claim 1, used as a blood pump.

12. A magnetically levitated pump, comprising:
a pump unit including a disk-shaped impeller for feeding liquid;
a magnetic bearing unit provided opposite to one of end faces along an axial direction of said impeller; and
a casing unit provided opposite to the other of said end faces,
wherein said magnetic bearing unit includes:
rotary driving means for transmitting a rotational driving force to said impeller, and
an electro-magnet for said magnetic bearing,
said pump unit includes:
a soft magnetic member opposite to said electro-magnet provided on said one of said end faces of said impeller and provided opposite to said electro-magnet for said magnetic bearing, and
an impeller-side ferromagnetic body provided on the other of said end faces of said impeller,
said casing unit includes a casing-side ferromagnetic body provided opposite to said impeller-side ferromagnetic body and attracting said impeller toward said casing unit,
said electro-magnet for said magnetic bearing has a magnetizing current flowing therethrough controlled to balance an attractive force between said electro-magnet for said magnetic bearing and said soft magnetic member opposite to said electro-magnet, an attractive force between said impeller-side ferromagnetic body and said casing-side ferromagnetic body, a force acting on said impeller generated by said rotary driving means, and other disturbance influencing said impeller, and
a surface of said impeller-side ferromagnetic body opposite to said casing-side ferromagnetic body and a surface of said casing-side ferromagnetic body opposite to said impeller-side ferromagnetic body are adapted to have shapes mutually different from each other, so that an area of said surface of said impeller-side ferromagnetic body is smaller than an area of said surface of said casing-side ferromagnetic body.

* * * * *